(12) United States Patent
Dashore

(10) Patent No.: US 12,290,546 B1
(45) Date of Patent: May 6, 2025

(54) ANTIMICROBIAL COMPOSITIONS AND METHODS FOR MAKING AND USING THE SAME

(71) Applicant: Jodie A. Dashore, Marlboro, NJ (US)

(72) Inventor: Jodie A. Dashore, Marlboro, NJ (US)

(*) Notice: Subject to any disclaimer, the term of this patent is extended or adjusted under 35 U.S.C. 154(b) by 0 days.

(21) Appl. No.: 18/794,793

(22) Filed: Aug. 5, 2024

(51) Int. Cl.
*A61K 36/00* (2006.01)
*A61K 36/53* (2006.01)
*A61K 36/59* (2006.01)
*A61K 47/10* (2017.01)

(52) U.S. Cl.
CPC .............. *A61K 36/59* (2013.01); *A61K 36/53* (2013.01); *A61K 47/10* (2013.01)

(58) Field of Classification Search
CPC .................................................... A61K 36/59
See application file for complete search history.

(56) References Cited

U.S. PATENT DOCUMENTS

| | | |
|---|---|---|
| 5,629,319 A | 5/1997 | Luo et al. |
| 5,681,958 A | 10/1997 | Bierer |
| 5,906,825 A | 5/1999 | Seabrook, Jr. et al. |
| 7,972,635 B2 | 7/2011 | Seabrook, Jr. et al. |
| 8,597,789 B2 | 12/2013 | Schulz et al. |
| 8,846,114 B1 | 9/2014 | Makela et al. |
| 9,744,120 B2 | 8/2017 | Neigel |
| 10,010,080 B2 | 7/2018 | Neigel |
| 10,405,553 B1 | 9/2019 | Mason et al. |
| 2022/0110977 A1* | 4/2022 | Saadat Niaki Moghaddam .......... A61K 38/40 |

* cited by examiner

*Primary Examiner* — Qiuwen Mi
(74) *Attorney, Agent, or Firm* — Orbit IP, LLP

(57) ABSTRACT

Antimicrobial compositions and methods for making and using the same are disclosed. The compositions comprise an effective amount of one or more of a *Cryptolepis sanguinolenta* tincture, a *Sida acuta* tincture, a *Terminalia chebula* tincture, an *Alchornea cordifolia* tincture, a *Phyllanthus emblica* tincture, a *Curcuma longa* tincture, an *Olea europaea* tincture, an *Embelia ribes* tincture, a *Tinospora cordifolia* tincture, and an *Ocimum tenuiflorum* tincture.

6 Claims, 1 Drawing Sheet

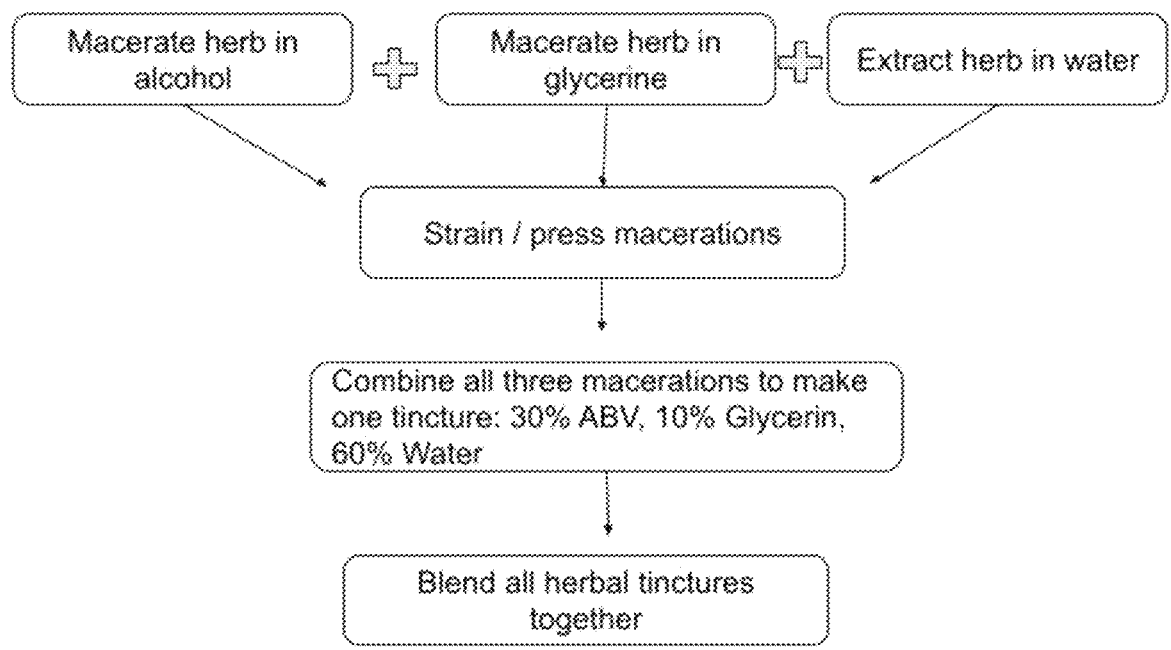

ANTIMICROBIAL COMPOSITIONS AND METHODS FOR MAKING AND USING THE SAME

FIELD OF THE INVENTION

This patent document relates generally to compositions and methods for treating microorganisms, and more particularly, to compositions and methods for making and using antimicrobial compositions.

DESCRIPTION OF THE RELATED ART

Bacterial infections are caused by microorganisms that can invade and multiply within the human body, leading to various health issues. These bacteria are broadly classified into two main categories: gram-positive and gram-negative, based on their cell wall structure. Gram-positive bacteria, such as *Staphylococcus aureus* and *Streptococcus pneumoniae*, have a thick peptidoglycan layer in their cell walls, which retains the crystal violet stain during the Gram staining process. On the other hand, gram-negative bacteria, like *Escherichia coli* and *Salmonella*, have a thinner peptidoglycan layer and an additional outer membrane, making them more resistant to certain antibiotics and harder to treat.

In addition to bacterial infections, fungal pathogens such as molds and yeasts can also cause significant health problems. Molds are multicellular fungi that form filamentous structures, while yeasts are single-celled fungi. These fungal pathogens can be particularly problematic for individuals with weakened immune systems and may require different treatment approaches compared to bacterial infections.

The treatment of primary bacterial infections typically involves the use of specific antibiotics tailored to the causative pathogen. For instance, penicillin, cloxacillin, and erythromycin are commonly used to treat over 90% of gram-positive bacterial infections. However, these targeted treatments may have little to no impact on secondary or tertiary infections caused by different pathogens or antibiotic-resistant strains. This limitation can be particularly challenging in complex cases where multiple pathogens are present or when antibiotic resistance is a concern.

Antibiotic resistance is a growing problem in the treatment of bacterial infections. Bacteria can develop resistance to antibiotics through various mechanisms, such as modifying their cell walls, producing enzymes that deactivate antibiotics, or developing efflux pumps that expel antibiotics from their cells. This resistance can make infections more difficult to treat and may require the use of stronger, potentially more toxic antibiotics. The overuse and misuse of antibiotics have contributed to the rise of antibiotic-resistant bacteria, such as methicillin-resistant *Staphylococcus aureus* (MRSA).

Given the diverse nature of infectious agents and the increasing prevalence of antibiotic resistance, there is a growing need for innovative treatments with broad-spectrum applicability. Thus, the existing landscape of infection treatments lacks adequate solutions. The present disclosure addresses this deficiency by introducing novel compositions that enable effective treatment against various forms of pathogens, including bacteria, molds, and yeasts, while remaining safe for use in vulnerable populations such as children. These innovative compositions could potentially address the challenges of treating complex infections and reduce the risk of developing antibiotic resistance. Additionally, this broad-spectrum treatment may be particularly valuable in cases where secondary or tertiary infections are present, as it could target multiple pathogens simultaneously without the need for multiple, potentially harsh medications. The novel approach presented in this disclosure aims to fill a critical gap in current infection treatment options, offering a more comprehensive and patient-friendly solution to combat a wide range of pathogens.

SUMMARY

Compositions and methods of using the same to treat infections are disclosed herein. Embodiments of the present disclosure may include administering to a patient a therapeutically effective amount of a composition consisting essentially of *Cryptolepis sanguinolenta* extract, *Sida acuta* extract, *Terminalia chebula* extract, *Alchornea cordifolia* extract, *Phyllanthus emblica* extract, *Curcuma longa* extract, *Olea europaea* extract, and a solvent mixture consisting essentially of alcohol, glycerin and water. In one embodiment, the composition may further include *Embelia ribes* extract, *Tinospora cordifolia* extract, and *Ocimum tenuiflorum* extract.

In one embodiment, the antibiotic resistant microbes comprise gram positive bacteria, gram negative bacteria, yeast and mold. The gram positive bacteria may include MARCONS Biofilm 3+ (10), *Staph saprophyticus*, Beta Strep Group A, Beta Strep Group B. Beta Strep Group C, *Enterococcus faecalis*, *Step pneumoniae*, *Staph epidermidis*, Methicillin Resistant *Staph aureus*, *Bacillus* species, *Staph aureus*, and *Corynebacterium* species (2). The gram negative bacteria may include *Pseudomonas aeruginosa*, *Proteus mirablis*, *Acinetobacter baumannii*, *Stenotrophomonas maltophilia*, *Pseudomonas fluorescens*, *Enterobacter aerogenes*, *Pseudomonas oryzihabitans*, *E. coli*, *Serratia marcescens*, *Chryseobacterium indologenes*, and *Klebsiella oxytoca*. The yeast may include *Candida albicans*, *Candida parapsilosis*, *Candida rugosa*, *Candida tropicalis*, *Cryptococcus* species, *Rhodotorula mucilaginosa*, and *Cryptococcus albidus*. The mold may include *Mucor* species, *Penicillium* species, *Chrysosporium* species, *Monilia sitophilia*, *Bipolaris* species, and *Cladosporium* species. In another embodiment, the composition may be used to treat acne vulgaris. In yet another embodiment, the composition may be used to treat impetigo.

In a particular embodiment, the *Cryptolepis sanguinolenta* extract is in a solvent with a weight (g) to volume (ml) ratio of *Cryptolepis sanguinolenta* extract to solvent of about 1:15; the *Sida acuta* extract is in a solvent with a weight (g) to volume (ml) ratio of *Sida acuta* extract to solvent of about 1:15; the *Terminalia chebula* extract is in a solvent with a weight (g) to volume (ml) ratio of *Terminalia chebula* extract to solvent of about 1:12; the *Alchornea cordifolia* extract is in a solvent with a weight (g) to volume (ml) ratio of *Alchornea cordifolia* extract to solvent of about 1:12; the *Phyllanthus emblica* extract is in a solvent with a weight (g) to volume (ml) ratio of *Phyllanthus emblica* extract to solvent of about 1:12; the *Curcuma longa* extract is in a solvent with a weight (g) to volume (ml) ratio of *Curcuma longa* extract to solvent of about 1:6, and the *Olea europaea* extract is in a solvent with a weight (g) to volume (ml) ratio of *Olea europaea* extract to solvent of about 1:10. In another embodiment, the *Embelia ribes* extract is in a solvent with a weight to volume ratio of *Embelia ribes* extract to solvent of about 1:10, the *Tinospora cordifolia* extract is in a solvent with a weight to volume ratio of *Tinospora cordifolia* extract to solvent of about 1:15, and the

*Ocimum tenuiflorum* extract is in a solvent with a weight to volume ratio of *Ocimum tenuiflorum* extract to solvent of about 1:10.

In another embodiment, a composition useful for the treatment of gram positive bacteria, gram negative bacteria, yeast and mold is disclosed. The composition comprising a therapeutically effective amount of: a *Cryptolepis sanguinolenta* tincture with a weight (g) to volume (ml) of *Cryptolepis sanguinolenta* extract to solvent of about 1:15; a *Sida acuta* tincture with a weight (g) to volume (ml) of *Sida acuta* extract to solvent of about 1:15; a *Terminalia chebula* tincture with a weight (g) to volume (ml) of *Terminalia chebula* extract to solvent of about 1:12; an *Alchornea cordifolia* tincture with a weight (g) to volume (ml) of *Alchornea cordifolia* extract to solvent of about 1:12; a *Phyllanthus emblica* tincture with a weight (g) to volume (ml) of *Phyllanthus emblica* extract to solvent of about 1:12; a *Curcuma longa* tincture with a weight (g) to volume (ml) of *Curcuma longa* extract to solvent of about 1:6; and an *Olea europaea* tincture with a weight (g) to volume (ml) of *Olea europaea* extract to solvent of about 1:10. In other embodiments, the composition further includes an *Embelia ribes* tincture with a weight (g) to volume (ml) ratio of *Embelia ribes* extract to solvent of about 1:10; a *Tinospora cordifolia* tincture with a weight (g) to volume (ml) ratio of *Tinospora cordifolia* extract to solvent of about 1:15; and an *Ocimum tenuiflorum* tincture with a weight (g) to volume (ml) ratio of *Ocimum tenuiflorum* extract to solvent of about 1:10.

As can be appreciated, the composition may comprise an effective amount of one or more such tinctures. In yet another embodiment, the composition comprises an effective amount of one or more tinctures having the following weight to volume ratio. In particular embodiments, the range for the weight (g) to volume (ml) ratio of *Cryptolepis sanguinolenta* extract to solvent is about 1:30 or less; preferably from about 1:25 to about 1:5, and more preferably from about 1:20 to about 1:10. In another embodiment, the range for the weight (g) to volume (ml) ratio of *Sida acuta* extract to solvent is about 1:30 or less; preferably from about 1:25 to about 1:5, and more preferably from about 1:20 to about 1:10. In a further embodiment, the range for the weight (g) to volume (ml) ratio of *Terminalia chebula* extract to solvent is about 1:30 or less; preferably from about 1:20 to about 1:5, and more preferably from about 1:15 to about 1:10. In another embodiment, the range for the weight (g) to volume (ml) ratio of *Alchornea cordifolia* extract to solvent is about 1:30 or less; preferably from about 1:20 to about 1:5, and more preferably from about 1:15 to about 1:10. Similarly, in another embodiment, the range for the weight (g) to volume (ml) ratio of *Phyllanthus emblica* extract to solvent is about 1:30 or less; preferably from about 1:20 to about 1:5, and more preferably from about 1:15 to about 1:10. Further, in a certain embodiment, the range for the weight (g) to volume (ml) ratio of *Curcuma longa* extract to solvent is about 1:20 or less; preferably from about 1:15 to about 1:2, and more preferably from about 1:10 to about 1:4. In one embodiment, the range for the weight (g) to volume (ml) ratio of *Olea europaea* extract to solvent is about 1:25 or less; preferably from about 1:20 to about 1:4, and more preferably from about 1:15 to about 1:7. Similarly, the range for the weight (g) to volume (ml) ratio of *Embelia ribes* extract to solvent may be about 1:25 or less; preferably from about 1:20 to about 1:4, and more preferably from about 1:15 to about 1:7. In particular embodiments, the range for the weight (g) to volume (ml) ratio of *Tinospora cordifolia* extract to solvent is about 1:30 or less; preferably from about 1:25 to about 1:5, and more preferably from about 1:20 to about 1:10. Finally, the range for the weight (g) to volume (ml) ratio of *Ocimum tenuiflorum* extract to solvent may be about 1:25 or less; preferably from about 1:20 to about 1:4, and more preferably from about 1:15 to about 1:7.

Each of the foregoing various aspects, together with those set forth in the claims and described in connection with the embodiments summarized above and disclosed herein may be combined to form claims for a composition, methods of manufacture and/or use in any way disclosed herein without limitation.

BRIEF DESCRIPTION OF THE DRAWINGS

These and other features, aspects and advantages are described below with reference to the drawings, which are intended to illustrate but not to limit the present disclosure. In the drawings, like reference characters denote corresponding features consistently throughout similar embodiments.

FIG. 1 is a flowchart depicting a method of making an antimicrobial composition, according to an embodiment of the present disclosure.

DETAILED DESCRIPTION

The compositions disclosed in the present disclosure are useful in medical applications for treating or preventing a variety of infections, such as but not limited to, those caused by gram positive bacteria, gram negative bacteria, yeast and mold. Although embodiments of these compositions (and methods for making and using the same) are disclosed herein, it is to be expressly understood that the present invention is not restricted solely to such embodiments. Rather, the present disclosure is directed to each of the inventive features described below, both individually as well as collectively, in various embodiments. Those of skill in the art will recognize that there are numerous variations and modifications of the disclosed inventions that are encompassed by its scope. Accordingly, the description of one or more embodiments should not be deemed to limit the scope of the present disclosure.

In one embodiment, novel compositions and methods for treating an infection caused by antibiotic resistant microbes are disclosed. As can be appreciated, antibiotic resistant microns such as gram positive bacteria are resistant to more than one class of antibiotics. The novel methods treat such antibiotic resistant microbes without the use of antibiotics. Such methods employ the use of a novel composition that includes *Cryptolepis sanguinolenta* extract, *Sida acuta* extract, *Terminalia chebula* extract, *Alchornea cordifolia* extract, *Phyllanthus emblica* extract, *Curcuma longa* extract, *Olea europaea* extract, and a solvent mixture of alcohol, glycerin and/or water. In another embodiment, the novel composition further includes *Embelia ribes* extract, *Tinospora cordifolia* extract, and *Ocimum tenuiflorum* extract.

In one embodiment, the *Cryptolepis sanguinolenta* extract may be in a solvent with a weight (g) to volume (ml) ratio of *Cryptolepis sanguinolenta* extract to solvent of about 1:15. In another embodiment, the *Sida acuta* extract may be in a solvent with a weight (g) to volume (ml) ratio of *Sida acuta* extract to solvent of about 1:15. Further, in a particular embodiment, the *Terminalia chebula* extract may be in a solvent with a weight (g) to volume (ml) ratio of *Terminalia chebula* extract to solvent of about 1:12. In another embodiment, the *Alchornea cordifolia* extract may be in a solvent with a weight (g) to volume (ml) ratio of *Alchornea cordifolia* extract to solvent of about 1:12. In yet another embodiment, the *Phyllanthus emblica* extract may be in a solvent with a weight (g) to volume (ml) ratio of *Phyllanthus emblica* extract to solvent of about 1:12. In another particular embodiment, the *Curcuma longa* extract may be in a solvent with a weight (g) to volume (ml) ratio of *Curcuma longa* extract to solvent of about 1:6. Further, the *Olea europaea* extract may be in a solvent with a weight (g) to volume (ml) ratio of *Olea europaea* extract to solvent of about 1:10.

In another embodiment, the novel composition further includes *Embelia ribes* extract, *Tinospora cordifolia* extract, and *Ocimum tenuiflorum* extract. The *Embelia ribes* extract may be in a solvent with a weight to volume ratio of *Embelia ribes* extract to solvent of about 1:10. The *Tinospora cordifolia* extract may be in a solvent with a weight to volume ratio of *Tinospora cordifolia* extract to solvent of about 1:15, and the *Ocimum tenuiflorum* extract may be in a solvent with a weight to volume ratio of *Ocimum tenuiflorum* extract to solvent of about 1:10.

Artisans skilled in the art would appreciate that numerous variations and modifications of the disclosed composition are within the scope of the present disclosure, including compositions with a combination of any two of the ten disclosed extracts. In other embodiments, the novel compositions have any three of the ten disclosed extracts. In yet other embodiments, the novel compositions have four or more of the ten disclosed extracts.

As can be appreciated, the magnitude of a therapeutic dose of the novel composition can vary with a particular cause of the condition, the severity of the condition, and the route of administration. The dose and/or the dose frequency can also vary according to the age, body weight, and response of an individual patient. For example, for a pediatric 5-year-old patient that is 32 pounds with confirmed lab positive MARCONs infection, the novel composition may be administered by providing 1-10 drops at 1-3 times per day after food in 0.5 oz of filtered/distilled water. In one embodiment, 1 drop may be administered once a day, next day 1 drop twice a day, next day 1 drop three-times a day, next day 2 drops once a day, next day 2 drops twice a day, next day 2 drops three times a day and so on until a dosage of 10 drops three times a day is reached. Skilled clinicians and physicians would appreciate that there are various factors to consider in administering the novel compositions, including age, bodyweight, symptoms, severity, clinical presentations, comorbidities, and lab results, among others. In one embodiment, for a very sensitive patient, the same prescription can be for topical application in the beginning and once the maximum dosage is achieved topically, then the patient may be ready for oral usage using a similar protocol. In other embodiment, for a severe patient, the novel compositions may be simultaneously administered topically and orally.

In one embodiment, the weight to volume ratio for each extract is above-specified ratio or less. For example, the weight to volume ratio of *Cryptolepis sanguinolenta* is about 1:15 or less, such as about 1:14, 1:13, 1:12, 1:11, 1:10, 1:09, 1:08, 1:07, 1:06, 1:05, 1:04, 1:03, 1:02, or 1:01 or less. In certain embodiments, however, dosages may include a ratio of about 1:15 or greater, such as about 1:16, 1:17, 1:18, 1:19, 1:20, 1:21, 1:22, 1:23, 1:24, 1:25 or greater.

In another embodiment, the weight to volume ratio of *Sida acuta* is about 1:15 or less, such as about 1:14, 1:13, 1:12, 1:11, 1:10, 1:09, 1:08, 1:07, 1:06, 1:05, 1:04, 1:03, 1:02, or 1:01 or less. In certain embodiments, however, dosages may include a ratio of about 1:15 or greater, such as about 1:16, 1:17, 1:18, 1:19, 1:20, 1:21, 1:22, 1:23, 1:24, 1:25 or greater. In another embodiment, the weight to volume ratio of *Terminalia chebula* is about 1:12 or less, such as about 1:11, 1:10, 1:09, 1:08, 1:07, 1:06, 1:05, 1:04, 1:03, 1:02, or 1:01 or less. In certain embodiments, however, dosages may include a ratio of about 1:12 or greater, such as about 1:13, 1:14, 1:15, 1:16, 1:17, 1:18, 1:19, 1:20, 1:21, 1:22, 1:23, 1:24, 1:25 or greater. In yet another embodiment, the weight to volume ratio of *Alchornea cordifolia* is about 1:12 or less, such as about 1:11, 1:10, 1:09, 1:08, 1:07, 1:06, 1:05, 1:04, 1:03, 1:02, or 1:01 or less. In certain embodiments, however, dosages may include a ratio of about 1:12 or greater, such as about 1:13, 1:14, 1:15, 1:16, 1:17, 1:18, 1:19, 1:20, 1:21, 1:22, 1:23, 1:24, 1:25 or greater. Further, the weight to volume ratio of *Phyllanthus emblica* may be about 1:12 or less, such as about 1:11, 1:10, 1:09, 1:08, 1:07, 1:06, 1:05, 1:04, 1:03, 1:02, or 1:01 or less. In certain embodiments, however, dosages may include a ratio of about 1:12 or greater, such as about 1:13, 1:14, 1:15, 1:16, 1:17, 1:18, 1:19, 1:20, 1:21, 1:22, 1:23, 1:24, 1:25 or greater. In particular embodiments, the weight to volume ratio of *Olea europaea* may be about 1:6 or less, such as about 1:05, 1:04, 1:03, 1:02, or 1:01 or less. In certain embodiments, however, dosages may include a ratio of about 1:06 or greater, such as about 1:07, 1:08, 1:09, 1:10, 1:11, 1:12, 1:13, 1:14, 1:15, 1:16, 1:17, 1:18, 1:19, 1:20, 1:21, 1:22, 1:23, 1:24, 1:25 or greater. In certain embodiments, the weight to volume ratio of *Embelia ribes* may be about 1:10 or less, such as about 1:09, 1:08, 1:07, 1:06, 1:05, 1:04, 1:03, 1:02, or 1:01 or less. In other embodiments, however, dosages may include a ratio of about 1:10 or greater, such as about 1:11, 1:12, 1:13, 1:14, 1:15, 1:16, 1:17, 1:18, 1:19, 1:20, 1:21, 1:22, 1:23, 1:24, 1:25 or greater. In another embodiment, the weight to volume ratio of *Tinospora cordifolia* is about 1:15 or less, such as about 1:14, 1:13, 1:12, 1:11, 1:10, 1:09, 1:08, 1:07, 1:06, 1:05, 1:04, 1:03, 1:02, or 1:01 or less. In certain embodiments, however, dosages may include a ratio of about 1:15 or greater, such as about 1:16, 1:17, 1:18, 1:19, 1:20, 1:21, 1:22, 1:23, 1:24, 1:25 or greater. Further, in certain embodiments, the weight to volume ratio of *Ocimum tenuiflorum* may be about 1:10 or less, such as about 1:09, 1:08, 1:07, 1:06, 1:05, 1:04, 1:03, 1:02, or 1:01 or less. In other embodiments, however, dosages may include a ratio of about 1:10 or greater, such as about 1:11, 1:12, 1:13, 1:14, 1:15, 1:16, 1:17, 1:18, 1:19, 1:20, 1:21, 1:22, 1:23, 1:24, 1:25 or greater.

Other embodiments include desired ranges for the weight to volume ratio for one or more of the ten extracts. In particular embodiments, the range for the weight (g) to volume (ml) ratio of *Cryptolepis sanguinolenta* extract to solvent is about 1:30 or less; preferably from about 1:25 to about 1:5, and more preferably from about 1:20 to about 1:10. In another embodiment, the range for the weight (g) to volume (ml) ratio of *Sida acuta* extract to solvent is about 1:30 or less; preferably from about 1:25 to about 1:5, and more preferably from about 1:20 to about 1:10. In a further embodiment, the range for the weight (g) to volume (ml) ratio of *Terminalia chebula* extract to solvent is about 1:30 or less; preferably from about 1:20 to about 1:5, and more preferably from about 1:15 to about 1:10. In another embodiment, the range for the weight (g) to volume (ml) ratio of *Alchornea cordifolia* extract to solvent is about 1:30 or less; preferably from about 1:20 to about 1:5, and more preferably from about 1:15 to about 1:10. Similarly, in another embodiment, the range for the weight (g) to volume (ml) ratio of *Phyllanthus emblica* extract to solvent is about 1:30 or less; preferably from about 1:20 to about 1:5, and more preferably from about 1:15 to about 1:10. Further, in a certain embodiment, the range for the weight (g) to volume (ml) ratio of *Curcuma longa* extract to solvent is about 1:20 or less; preferably from about 1:15 to about 1:2, and more preferably from about 1:10 to about 1:4. In one embodiment, the range for the weight (g) to volume (ml) ratio of *Olea europaea* extract to solvent is about 1:25 or less; preferably from about 1:20 to about 1:4, and more preferably from about 1:15 to about 1:7. Similarly, the range for the weight (g) to volume (ml) ratio of *Embelia ribes* extract to solvent may be about 1:25 or less; preferably from about 1:20 to about 1:4, and more preferably from about 1:15 to about 1:7. In particular embodiments, the range for the weight (g) to volume (ml) ratio of *Tinospora cordifolia* extract to solvent is about 1:30 or less; preferably from about 1:25 to about 1:5, and more preferably from about 1:20 to about 1:10. Finally, the range for the weight (g) to volume (ml) ratio of *Ocimum tenuiflorum* extract to solvent may be about 1:25 or less; preferably from about 1:20 to about 1:4, and more preferably from about 1:15 to about 1:7.

In some embodiments, the desired ranges for the weight to volume ratio for one or more of the ten extracts may be outside of the ranges set forth above. Further, an ordinary skilled clinician or treating physician may adjust or terminate therapy in consideration of individual patient response.

In one embodiment, the extracts are from organically grown herbs. The herb extracts may be dry or fresh extracts and may be obtained from a plant root, leaf, stem or fruit. In one embodiment, the *Cryptolepis sanguinolenta* extract may be a dry root from the *Cryptolepis sanguinolenta* plant species, *Sida acuta* extract may be a dry leaf and/or stem from the *Sida acuta* plant species, *Terminalia chebula* extract may be a dry fruit powder from a Haritaki *Terminalia chebula* plant species, *Alchornea cordifolia* extract may be a dry leaf and/or stem from the *Alchornea cordifolia* plant species, *Phyllanthus emblica* extract may be a dry fruit from the *Phyllanthus emblica* (amla) plant species, *Curcuma longa* extract may be a fresh root (Tumeric) from the *Curcuma longa* plant species, *Olea europaea* extract may be a dry leaf from olive tree or shrub species, *Embelia ribes* extract may be a dry leaf from the *Embelia ribes* (vidanga) plant species, *Tinospora cordifolia* extract may be a dry root from the *Tinospora cordifolia* (guduchi) plant species, and *Ocimum tenuiflorum* extract may be a dry leaf and/or stem from the *Ocimum tenuiflorum* (tulsi) plant species.

The solvents used to prepare tincture for each extract may include organic alcohol, such as organic cane alcohol. In another embodiment, the solvent is a mixture that further includes organic vegetable glycerin and spring water. Other examples of suitable solvents include, but not limited to, ethers, such as diethyl ether, disopropyl ether, tetrahydrofuran, MTBE, dioxane, and dimethoxyethane; alcohols, such as methanol, ethanol, ethylene glycol, 1-propanol, 2-propanol, 2-methoxyethanol, 1-butanol, 2-butanol, iso-butyl alcohol, t-butyl alcohol, glycerol, and C1-C6 alcohols; halogenated hydrocarbons, such as dichloromethane, chloroform, carbon tetrachloride, and chlorobenzene; aromatic hydrocarbons, such as toluene; aliphatic hydrocarbons, nitriles, esters and polar aprotic solvents such as DMF, DMSO, Dimethylacetamide (DMAc), water; any mixtures of two or more thereof. As can be appreciated, other agents may be used to prepare the tincture for one or more of the herb extracts.

In one embodiment, the present disclosure further provides a method for making the novel composition, as illustrated in the exemplary FIG. 1. The method includes preparing a tincture for a particular extract. In one embodiment, the preparation of the tincture includes macerating a first quantity of the herb in alcohol (such as 45% organic cane alcohol by volume) (100). The tincture preparation may also include macerating a second quantity of the herb in glycerin-based solvent, such as organic vegetable glycerin (110), and heating the glycerin-based solvent at high temperature, i.e., about 145-160 degrees, for a certain period, such as 180 minutes (120). In another embodiment, the tincture preparation may also include decocting or infusing a third quantity of the herb in water, such as natural spring water, for a certain period (130). Next, each maceration is strained and/or pressed (140) and then combined to make a tincture containing the first, second, and third quantities of the herb contained in a mixture of alcohol, glycerin-based solvent and water (150). Finally, the tincture for the particular extracts are combined and blended together to form the desired novel composition (160).

A study was conducted to evaluate the effectiveness of the novel compositions on several cultured organisms. Table 1 lists the organisms tested.

TABLE 1

Gram Positive Bacteria:

1. MARCONS Biofilm 3+ (10)
2. *Staph saprophyticus*
3. Beta Strep Group A
4. Beta Strep Group B
5. Beta Strep Group C
6. *Enterococcus faecalis*
7. Step pneumoniae
8. Staph epidermidis
9. Methicillin Resistant *Staph aureus*
10. *Bacillus* species
11. *Staph aureus*
12. *Corynebacterium* species (2)

Gram Negative Bacteria:

1. *Pseudomonas aeruginosa*
2. *Proteus mirablis*
3. *Acinetobacter baumannii*
4. *Stenotrophomonas maltophilia*
5. *Pseudomonas fluorescens*
6. *Enterobacter aerogenes*
7. *Pseudomonas oryzihabitans*
8. *E.coli*
9. *Serratia marcescens*
10. *Chryseobacterium indologenes*
11. *Klebsiella oxytoca*

Yeast:

1. *Candida albicans*
2. *Candida parapsilosis*
3. *Candida rugosa*
4. *Candida tropicalis*
5. *Cryptococcus* species
6. *Rhodotorula mucilaginosa*
7. *Cryptococcus albidus*

Mold:

1. *Mucor* species
2. *Penicillium* species
3. *Chrysosporium* species
4. *Monilia sitophilia*
5. *Bipolaris* species
6. *Cladosporium* species The novel composition included extracts from ten plant species: (1) *Cryptolepis sanguinolenta*, (2) *Sida acuta*, (3) *Terminalia chebula*, (4) *Alchornea cordifolia*, (5) *Phyllanthus emblica*, (6) *Curcuma longa*, (7) *Olea europaea*, (8) *Embelia ribes*, (9) *Tinospora cordifolia*, and (10) *Ocimum tenuiflorum*.

The preparation of a tincture for each extract is described next. For *Cryptolepis sanguinolenta*, about 21 g of the dry root was macerated in about 315 ml alcohol (i.e. 45% organic cane alcohol). About 3 g of the dry root was also macerated in about 50 ml of organic vegetable glycerin, which was then heated for about 180 minutes at about 145-160 degrees. Further, about 7 g of the dry root was decocted in about 109 ml of spring water for 20 minutes and allowed to steep for about 60 minutes. Then, all three macerations were combined to form one tincture for *Cryptolepis sanguinolenta*.

For *Sida acuta*, about 15 g of its dry leaf and stem was macerated in about 236 ml alcohol (i.e. 60% organic cane alcohol). About 3 g of its dry leaf and stem was also macerated in about 50 ml of organic vegetable glycerin, which was then heated for about 180 minutes at about 145-160 degrees. Further, about 12 g of its dry leaf and stem was infused in about 188 ml of hot spring water for about 120 minutes. Then, all three macerations were combined to form one tincture for *Sida acuta*.

For *Terminalia chebula*, about 19 g of its dry fruit powder was macerated in about 236 ml alcohol (i.e. 60% organic cane alcohol). About 4 g of its dry fruit powder was also macerated in about 50 ml of organic vegetable glycerin, which was then heated for about 180 minutes at about 145-160 degrees. Further, about 15 g of its dry fruit powder was decocted in about 188 ml of spring water for 20 minutes and allowed to steep for about 60 minutes. Then, all three macerations were combined to form one tincture for *Terminalia chebula*.

For *Alchornea cordifolia*, about 23 g of its dry leaf and stem was macerated in about 283 ml alcohol (i.e. 50% organic cane alcohol). About 4 g of its dry leaf and stem was also macerated in about 50 ml of organic vegetable glycerin, which was then heated for about 180 minutes at about 145-160 degrees. Further, about 11 g of its dry leaf and stem was infused in about 141 ml of hot spring water for about 120 minutes. Then, all three macerations were combined to form one tincture for *Alchornea cordifolia*.

For *Phyllanthus emblica*, about 33 g of its dry fruit powder was macerated in about 405 ml alcohol (i.e. 35% organic cane alcohol). About 4 g of its dry fruit powder was also macerated in about 50 ml of organic vegetable glycerin, which was then heated for about 180 minutes at about 145-160 degrees. Further, about 2 g of its dry fruit powder was decocted in about 119 ml of spring water for 20 minutes and allowed to steep for about 60 minutes. Then, all three macerations were combined to form one tincture for *Phyllanthus emblica*.

For *Curcuma longa*, about 39 g of its fresh root was macerated in about 236 ml alcohol (i.e. 60% organic cane alcohol). About 8 g of its fresh root was also macerated in about 50 ml of organic vegetable glycerin, which was then heated for about 180 minutes at about 145-160 degrees. Further, about 31 g of its fresh root was decocted in about 188 ml of spring water for 20 minutes and allowed to steep for about 60 minutes. Then, all three macerations were combined to form one tincture for *Curcuma longa*.

For *Olea europaea*, about 40 g of its dry leaf was macerated in about 405 ml alcohol (i.e. 35% organic cane alcohol). About 4 g of its dry leaf was also macerated in about 50 ml of organic vegetable glycerin, which was then heated for about 180 minutes at about 145-160 degrees. Further, about 2 g of its dry leaf was infused in about 19 ml of hot spring water for about 120 minutes. Then, all three macerations were combined to form one tincture for *Olea europaea*.

For *Embelia ribes*, about 23 g of its dry leaf was macerated in about 236 ml alcohol (i.e. 60% organic cane alcohol). About 4 g of its dry leaf was also macerated in about 50 ml of organic vegetable glycerin, which was then heated for about 180 minutes at about 145-160 degrees. Further, about 18 g of its dry leaf was infused in about 188 ml of hot spring water for about 120 minutes. Then, all three macerations were combined to form one tincture for *Embelia ribes*.

For *Ocimum tenuiflorum*, about 29 g of its dry leaf and stem was macerated in about 354 ml alcohol (i.e. 40% organic cane alcohol). About 4 g of its dry leaf and stem was also macerated in about 50 ml of organic vegetable glycerin, which was then heated for about 180 minutes at about 145-160 degrees. Further, about 5 g of its dry leaf and stem was infused in about 70 ml of hot spring water for about 120 minutes. Then, all three macerations were combined to form one tincture for *Ocimum tenuiflorum*.

For *Tinospora cordifolia*, about 27 g of its dry root was macerated in about 405 ml alcohol (i.e. 35% organic cane alcohol). About 3 g of its dry root was also macerated in about 50 ml of organic vegetable glycerin, which was then heated for about 180 minutes at about 145-160 degrees. Further, about 2 g of its dry root was decocted in about 19 ml of spring water for 20 minutes and allowed to steep for about 60 minutes. Then, all three macerations were combined to form one tincture for *Tinospora cordifolia*.

All ten herb tinctures were then combined and stirred together for about 3 minutes to form a novel composition, according to one embodiment of the present disclosure. The exemplary final blend for the study has the breakdown of herb tinctures by volume set forth in Table 2 below.

TABLE 2

| | |
|---|---|
| *cryptolepis sanguinolenta* tincture | about 12.49% of total volume |
| *sida acuta* tincture | about 12.49% of total volume |
| *terminalia chebula* tincture | about 12.49% of total volume |
| *alchornea cordifolia* tincture | about 12.49% of total volume |
| *phyllanthus emblica* tincture | about 12.49% of total volume |
| *curcuma longa* tincture | about 12.49% of total volume |
| *olea europaea* tincture | about 12.49% of total volume |
| *embelia ribes* tincture | about 4.16% of total volume |
| *tinospora cordifolia* tincture | about 4.16% of total volume |
| *ocimum tenuiflorum* tincture | about 4.16% of total volume |

As can be appreciated, the study implemented several testing protocols to ensure validity and accuracy of the results. First, all testing was performed with a patient control. Second, a McFarland Standard (MS) of 1.0 was prepared for the testing of Multiple Antibiotic Resistant Coagulase Negative *Staphylococcus* (MARCONS) and all other organisms. Third, all testing was performed in a liquid format.

For each patient culture, 2 polystyrene tubes 12×75 mm were labeled as test and control. For each patient and its control, the MS of 1.0, 100 µl was pipetted into 900 µl of Tryptic Soy Broth (TSB) or Sabouraud Dextrose Broth for mold and yeast. Then, the 1000 µl of test solution for the patient test was pipetted and 1000 µl of water for each patient control tube were pipetted for testing. Both sets of patient tubes were incubated for 24 hours at 37° C. The mold and yeast tubes were incubated at room temperature for 2-6 days because they take longer to grow. After the incubation period, the tubes (test and control) were removed from the incubator and a 1 µl loop was taken for the bacteria and planted on a Blood Agar Plate (BAP). A swab was taken for Mold and Yeast testing and applied to Sabouraud Dextrose Agar plates which were incubated at 37° C. or room temperature for 2-6 days. Then growth was evaluated for each patient test compared to its own control.

As can be appreciated, various dosage concentrations of the novel composition may be adopted and implemented within the scope of the present disclosure. In this study, and according to one particular embodiment, the dosage adopted and implemented was about twice the dosage concentration of the novel composition. The dosage concentration was increased to take into consideration the dilution effect in the testing protocol. Persons skilled in the art would appreciate that the testing values used were such that the final concentration in-vitro was about equal to a treatment nasal spray concentration.

The study unexpectedly revealed that all MARCONS, gram positive bacteria, gram negative bacteria, yeast and mold showed complete inhibition showing. No Growth for each test compared to each patient control. As such, the novel formulation was able to treat and eradicate nares MARCONS and other micro-organisms.

Another study was performed on a patient with impetigo, applying the novel composition topically on the skin. Impetigo, also known as impetiginous dermatitis, is a secondary infection of preexisting skin disease or traumatized skin. It is caused by *Staphylococcus aureus*, group A beta hemolytic streptococci (GABHS, also known as *Streptococcus pyogenes*), or a combination of both, The objective of the study was to evaluate the safety and efficacy of the novel composition for the treatment of impetigo infection. The study was performed on a 5-year-old male child with repeated flare ups of chronic persistent, antibiotic resistant, impetigo. Multiple rounds of different antibiotics were previously administered but had minimal impact and recurrence every 1-2 months. The novel composition (described in the prior study) was applied by the parent on a trial basis. The study involved applying the novel composition by gently massaging in 2-3 drops on the lesions 2-3×/day using a clean finger or Q-tip. Reduction in pain and discomfort were observed and reported within 24 hours and complete eradication were observed and reported within 4 days of usage. The impetigo has since not returned. The results of the study demonstrate that the novel compositions, in accordance with embodiments of the present disclosure, are effective in treating impetigo.

In yet another study, the novel composition was topically applied on the skin of a patient with acne vulgaris. Acne vulgaris is a common skin condition that occurs when hair follicles become clogged with oil, bacteria, and skin cells. It's characterized by the formation of comedones, papules, pustules, nodules, and/or cysts and can cause symptoms such as blackheads, whiteheads, pimples, and painful nodules under the skin. Acne vulgaris typically affects areas of the skin with the most sebaceous follicles, such as the face, upper chest, and back. Local symptoms may include pain, tenderness, or erythema.

The objective of the study was to evaluate the safety and efficacy of the novel composition for the treatment of acne vulgaris. The study was performed on a 24-year-old female with chronic cystic acne on cheeks, chin, upper back and underarms/axilla. Multiple rounds of different antibiotics were previously administered but had minimal impact. The novel composition (described in the prior study) was applied by the patient on a trial basis. The study involved applying the novel composition by gently massaging in 2-3 drops on the lesions 2-3×/day using a clean finger or Q-tip. Reduction in pain and discomfort were observed and reported within 24 hours and complete eradication was observed and reported within 7 days of usage. The results of the study demonstrate that the novel compositions, in accordance with embodiments of the present disclosure, are effective in treating acne vulgaris. The patient additionally decided to incorporate oral usage with 10 drops diluted in filtered water 3×/day ongoing.

In one embodiment, the novel formulation may be implemented for nasal spray applications. In another embodiment, the novel formulation may be administered for topical use, such as through an application of liquid, cream, lotion, soap, foam or body wash on a patient's skin. In yet another embodiment, the novel formulation may be administered orally. Other suitable route of administration can be employed for providing the patient was an effective dosage of a novel composition, according to an embodiment of the present disclosure. For example, oral, rectal, transdermal, parenteral, topical, inhalable, and like forms of administration can be employed. Suitable dosage forms include tablets, suspensions, aerosol sprays, solutions, capsules, patches, lotions and the like. Formulations of the disclosed embodiments can contain a mixture of the active compound extracts with pharmaceutically acceptable carriers or dilutants.

As can be appreciated, one aspect of the present disclosure is the ability to treat and eradicate a wide array of infectious microorganisms, including gram positive bacteria, gram negative bacteria, yeast and mold. As patients often have secondary and/or tertiary infections with different strains of bacteria, the novel formulation provides an optimal treatment with antimicrobial active botanical compounds to eradicate not only the primary cause of infections, but also other secondary and/or tertiary ones too.

In one embodiment, the novel compositions and methods for making and using the same allow for optimal bio availability of the herbals in an efficient, cost effective and eco conscious manner. The herbs have multiple beneficial and antimicrobial botanical active compounds present. As such, there is little to no resistance to the novel composition. Indeed, there are no known documented studies citing a patient having developed resistance to an herbal supplement. In contrast, a patient can develop resistance to one or more antibiotics, as documented in several studies.

In another aspect of the present disclosure, the novel composition creates multiple continuous flow of treatment with specific herbs chosen for their optimally effective mechanism of action, tissue penetration, and tissue healing properties delivered in an easy to administer form of liquid oral drops or topical skin application. As can be appreciated, the novel composition in specific embodiments is non-toxic and can be used for pediatrics and all age groups.

In certain embodiments of the present disclosure, the compounds and compositions can be used in combination therapy with at least one other therapeutic agent. The compound of the invention and the therapeutic agent can act additively or, more preferably, synergistically. In a preferred embodiment, a compound or a composition comprising a compound of the invention is administered concurrently with the administration of another therapeutic agent, which can be part of the same composition as the compound of the present disclosure or a different composition. In another embodiment, a compound or a composition comprising a compound of the present disclosure is administered prior or subsequent to administration of another therapeutic agent. As can be appreciated, one embodiment combination therapy involves alternating between administering a compound or a composition comprising a compound of the present disclosure and a composition comprising another therapeutic agent. The duration of administration of each drug or therapeutic agent can be, e.g., one week, two weeks, or one month.

Although the various inventive aspects are herein disclosed in the context of certain preferred embodiments, implementations, and examples, it will be understood by those skilled in the art that the present invention extends beyond the specifically disclosed embodiments to other alternative embodiments and/or uses of the invention and obvious modifications and equivalents thereof. In addition, while a number of variations of the inventive aspects have been shown and described in detail, other modifications, which are within their scope will be readily apparent to those of skill in the art based upon this disclosure. It should be also understood that the scope this disclosure includes the various combinations or sub-combinations of the specific features and aspects of the embodiments disclosed herein, such that the various features, modes of implementation, and aspects of the disclosed subject matter may be combined with or substituted for one another. Thus, it is intended that the scope of the present invention herein disclosed should not be limited by the particular disclosed embodiments or implementations described above, but should be determined only by a fair reading of the claims.

Similarly, this disclosure is not be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

Further, all claim terms should be interpreted in their most expansive forms so as to afford the applicant the broadest coverage legally permissible. Although the embodiments have been described with reference to the drawings and specific examples, it will readily be appreciated by those skilled in the art that many modifications and adaptations of the processes, methods and apparatuses described herein are possible without departure from the spirit and scope of the embodiments as claimed herein. Thus, it is to be clearly understood that this description is made only by way of example and not as a limitation on the scope of the embodiments as claimed below.

What is claimed is:

1. A composition useful for the treatment of gram positive bacteria, gram negative bacteria, yeast and mold, the composition comprising a therapeutically effective amount of:
    a *Cryptolepis sanguinolenta* tincture with a weight (g) to volume (ml) of *Cryptolepis sanguinolenta* extract to solvent of about 1:15;
    a *Sida acuta* tincture with a weight (g) to volume (ml) of *Sida acuta* extract to solvent of about 1:15;
    a *Terminalia chebula* tincture with a weight (g) to volume (ml) of *Terminalia chebula* extract to solvent of about 1:12;
    an *Alchornea cordifolia* tincture with a weight (g) to volume (ml) of *Alchornea cordifolia* extract to solvent of about 1:12;
    a *Phyllanthus emblica* tincture with a weight (g) to volume (ml) of *Phyllanthus emblica* extract to solvent of about 1:12;
    a *Curcuma longa* tincture with a weight (g) to volume (ml) of *Curcuma longa* extract to solvent of about 1:6; and
    an *Olea europaea* tincture with a weight (g) to volume (ml) of *Olea europaea* extract to solvent of about 1:10.

2. The composition of claim 1 further comprising a therapeutically effective amount of:
    an *Embelia ribes* tincture with a weight (g) to volume (ml) ratio of *Embelia ribes* extract to solvent of about 1:10;
    a *Tinospora cordifolia* tincture with a weight (g) to volume (ml) ratio of *Tinospora cordifolia* extract to solvent of about 1:15; and
    an *Ocimum tenuiflorum* tincture with a weight (g) to volume (ml) ratio of *Ocimum tenuiflorum* extract to solvent of about 1:10.

3. The composition of claim 1:
    wherein the gram positive bacteria comprises MARCONS Biofilm 3+ (10), *Staph saprophyticus*, Beta Strep Group A, Beta Strep Group B, Beta Strep Group C, *Enterococcus faecalis*, *Step pneumoniae*, *Staph epidermidis*, Methicillin Resistant *Staph aureus*, *Bacillus* species, *Staph aureus*, and *Corynebacterium* species (2);
    wherein the gram negative bacteria comprises *Pseudomonas aeruginosa*, *Proteus mirablis*, *Acinetobacter baumannii*, *Stenotrophomonas maltophilia* 5, *Pseudomonas fluorescens*, *Enterobacter aerogenes*, *Pseudomonas oryzihabitans*, *E. coli*, *Serratia marcescens*, *Chryseobacterium indologenes*, and *Klebsiella oxytoca*;
    wherein the yeast comprises *Candida albicans*, *Candida parapsilosis*, *Candida rugosa*, *Candida tropicalis*, *Cryptococcus* species, *Rhodotorula mucilaginosa*, *Cryptococcus albidus*; and
    wherein the mold comprises *Mucor* species, *Penicillium* species, *Chrysosporium* species, *Monilia sitophila*, *Bipolaris* species, and *Cladosporium* species.

4. The composition of claim 1, wherein each of the *Cryptolepis sanguinolenta* extract, the *Sida acuta* extract, the *Terminalia chebula* extract, the *Alchornea cordifolia* extract, the *Phyllanthus emblica* extract, the *Curcuma longa* extract, and the *Olea europaea* extract is about 12.5% of a total volume of the composition.

5. The composition of claim 1, wherein each of the *Embelia ribes* extract, the *Tinospora cordifolia* extract, and the *Ocimum tenuiflorum* extract is about 4.16% of a total volume of the composition.

6. The composition of claim 1, where in the solvent comprises alcohol, glycerin and water.

* * * * *